US012403227B2

(12) United States Patent
Jor (10) Patent No.: US 12,403,227 B2
(45) Date of Patent: Sep. 2, 2025

(54) CENTRALLY CONTROLLED MULTI-PATIENT DIALYSIS TREATMENT SYSTEM AND ITS USE

(71) Applicant: Fresenius Medical Care Deutschland GmbH, Bad Homburg (DE)

(72) Inventor: Kee Jor, Hong Kong (CN)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1042 days.

(21) Appl. No.: 17/261,662

(22) PCT Filed: Jul. 20, 2018

(86) PCT No.: PCT/CN2018/096358
§ 371 (c)(1),
(2) Date: Jan. 20, 2021

(87) PCT Pub. No.: WO2020/014937
PCT Pub. Date: Jan. 23, 2020

(65) Prior Publication Data
US 2021/0268160 A1    Sep. 2, 2021

(51) Int. Cl.
*A61M 1/16*    (2006.01)
*A61M 1/34*    (2006.01)
(Continued)

(52) U.S. Cl.
CPC ........ *A61M 1/1601* (2014.02); *A61M 1/1657* (2022.05); *A61M 1/1658* (2013.01);
(Continued)

(58) Field of Classification Search
CPC .............. A61M 1/1601; A61M 1/1657; A61M 1/1658; A61M 1/1662; A61M 1/1666;
(Continued)

(56) References Cited

U.S. PATENT DOCUMENTS

| 4,348,280 | A |   | 9/1982 | George et al. |
| 5,591,344 | A | * | 1/1997 | Kenley ............... A61M 1/1682 |
|           |   |   |        | 210/764 |

(Continued)

FOREIGN PATENT DOCUMENTS

| CN | 107715210 | 2/2018 |
| GB | 1501956   | 2/1978 |

(Continued)

OTHER PUBLICATIONS

Extended European Search Report in European Appln. No. 18927030.9, dated Feb. 10, 2022, 7 pages.
(Continued)

*Primary Examiner* — Pranav N Patel
(74) *Attorney, Agent, or Firm* — Fish & Richardson P.C.

(57) ABSTRACT

A centrally controlled multi-patient dialysis treatment system (1) as disclosed herein comprises: a dialysate preparation unit (2) configured to prepare a dialysate based on a prescription and control dialysate delivery for dialysis treatments in progress; one or more dialysate modules (3) configured to deliver the dialysate to a dialyzer (4) and control an ultrafiltration process; and one or more patient modules (5) configured to control an extracorporeal blood flow through the dialyzer (4) for the dialysis treatment, wherein the dialysate preparation unit (2), the dialysate modules (3) and the patient modules (5) are configured to be adapted to be assembled into an integrated dialysis treatment system suitable for one or more patients (6). Also an use of the centrally controlled multi-patient dialysis treatment system (1) for one or more patients' dialysis treatments is disclosed herein. For the centrally controlled multi-patient dialysis treatment system, in contrast to the conventional in-center dialysis infrastructures, in addition to cost saving, it is highly space efficient. Moreover, the centrally controlled (Continued)

multi-patient dialysis treatment system is robust and easy to setup.

17 Claims, 4 Drawing Sheets

(51) Int. Cl.
    *G16H 20/40*     (2018.01)
    *G16H 40/20*     (2018.01)
    *G16H 40/40*     (2018.01)
    *G16H 40/67*     (2018.01)

(52) U.S. Cl.
    CPC ........ *A61M 1/1662* (2014.02); *A61M 1/1666* (2014.02); *A61M 1/3413* (2013.01); *G16H 20/40* (2018.01); *G16H 40/20* (2018.01); *G16H 40/40* (2018.01); *G16H 40/67* (2018.01); *A61M 2205/502* (2013.01); *A61M 2205/84* (2013.01)

(58) Field of Classification Search
    CPC .......... A61M 1/3413; A61M 2205/502; A61M 2205/84; A61M 1/1635; A61M 1/166; A61M 1/1672; A61M 1/1686; A61M 1/169; A61M 1/3623; A61M 1/1656; A61M 1/14; G16H 20/40; G16H 40/20; G16H 40/40; G16H 40/67
    See application file for complete search history.

(56) References Cited

U.S. PATENT DOCUMENTS

| | | | |
|---|---|---|---|
| 5,647,984 | A | 7/1997 | Hovland et al. |
| 10,874,790 | B2 | 12/2020 | Gerber et al. |
| 2006/0052949 | A1 | 3/2006 | Fletcher-Haynes et al. |
| 2007/0276328 | A1 | 11/2007 | Childers et al. |
| 2009/0124963 | A1* | 5/2009 | Hogard ............... A61M 1/1635 604/30 |
| 2012/0175296 | A1* | 7/2012 | Wehmeyer .......... A61M 1/3622 210/321.71 |
| 2012/0308431 | A1* | 12/2012 | Kotsos ................ A61M 1/1686 422/105 |
| 2012/0318739 | A1 | 12/2012 | Kopperschmidt et al. |
| 2013/0020237 | A1 | 1/2013 | Wilt et al. |
| 2014/0276373 | A1 | 9/2014 | Minkus |
| 2015/0314055 | A1* | 11/2015 | Hogard ............... A61M 1/1672 210/232 |
| 2016/0101225 | A1 | 4/2016 | Smith et al. |

FOREIGN PATENT DOCUMENTS

| | | |
|---|---|---|
| JP | S51-065467 | 6/1976 |
| JP | H06-245995 | 9/1994 |
| JP | H11-506673 | 6/1999 |
| JP | 2003-175101 | 6/2003 |
| JP | 2004-000479 | 1/2004 |
| JP | 2013-017492 | 1/2013 |
| JP | 2013-512012 | 4/2013 |
| JP | 2014-004194 | 1/2014 |
| JP | 2014-111131 | 6/2014 |
| JP | 2014-524766 | 9/2014 |
| JP | 2016-512463 | 4/2016 |
| JP | 2018-082904 | 5/2018 |
| WO | WO 96/25214 | 8/1996 |
| WO | WO 00/12991 | 3/2000 |
| WO | WO 2005035023 | 4/2005 |
| WO | WO 2012166377 | 12/2012 |
| WO | WO 2015183981 | 12/2015 |
| WO | WO 2017158392 | 9/2017 |

OTHER PUBLICATIONS

PCT International Preliminary Report on Patentability in International Appln. No. PCT/CN2018/096358, mailed Feb. 4, 2021, 9 pages.

PCT International Search Report and Written Opinion in International Appln. No. PCT/CN2018/096358, mailed Apr. 25, 2019, 12 pages.

Office Action in Japanese Appln. No. 2021-502985, dated Oct. 18, 2023, 7 pages (English translation).

Office Action in Japanese Appln. No. 2021-502985, dated Aug. 2, 2022, 14 pages (with English translation).

Search Report in Japanese Appln. No. 2021-502985, dated Jul. 20, 2022, 35 pages (with English translation).

\* cited by examiner

CENTRALLY CONTROLLED MULTI-PATIENT DIALYSIS TREATMENT SYSTEM AND ITS USE

CROSS-REFERENCE TO RELATED APPLICATIONS

The present application is the national stage entry of International Patent Application No. PCT/CN2018/096358, filed on Jul. 20, 2018, the disclosure of which is incorporated herein by reference.

TECHNICAL FIELD

The disclosure relates to a centrally controlled multi-patient dialysis treatment system and a use of the centrally controlled multi-patient dialysis treatment system for one or more patients' dialysis treatments.

BACKGROUND ART

The number of end stage renal disease (ESRD) patients is increasing in particular in recent years. Hemodialysis, as an effective treatment method for the disease, is a procedure for removing toxic substances and metabolites normally removed by the kidneys, and for aiding in regulation of fluid and electrolyte balance. Hemodialysis is usually accomplished by a dialysis machine using dialysate.

However, only a relatively small fraction of ESRD patients can access to the dialysis treatments due to various factors. Treatment cost is very critical to the untapped market in which the patients are treated with the standard hemodialysis. Safety and efficiency are also crucial. Significant demand for the hemodialysis can be expected in the next 10 years in the lower tier hospitals in the emerging market. In these hospitals, acid and basic concentrates are usually prepared manually in an adjacent room and carried manually to each dialysis machine. The process is both labor intensive and the dialysate quality may be compromised.

As a more efficient and safer solution, at present, a central dialysis fluid delivery system (CDDS) is widely used to prepare and distribute the dialysate to a plurality of bedside dialysis machines, for example about 30-40 dialysis machines. The system simplifies the maintenance and supervision involved by combining management of the dialysate for a plurality of patients, preparation of cleaning and antiseptic solutions, and delivery of these solutions to each bedside dialysis machine. Such a system has been used for many years. It is usually more cost-efficient for a large number of patients, for example 20 or more. However, a malfunction may affect all patients and there is a constant risk of contamination due to a long dialysis piping.

Moreover, some parts of the system are normally installed in an isolated equipment room at a distance from treatment area and the bedside dialysis machines used in the system are typically standard hemodialysis machines only with dialysate mixing devices removed such that the bedside dialysis machines have unchanged footprint. However, the equipment room needs have more space to accommodate acid and basic power-mixing devices and a central dialysate preparation unit. In addition, each bedside dialysis machine has a dialysate line connection of about 2 meters such that a small endotoxin retentive filter (ETRF) is needed to go with each dialysis machine for hygiene control, in addition to a main ETRF.

Furthermore, the lower tier hospitals are smaller with limited capabilities and infrastructure, but it is costly, time consuming and space-consuming to plan and set up a new system. The known systems are not suitable well to deliver cost-efficient treatment solution. Therefore, an improved system is needed to overcome at least one of the above problems.

SUMMARY OF THE DISCLOSURE

In view of the problems existing in the prior art, an object of the disclosure is to provide a centrally controlled multi-patient dialysis treatment system and a use of the centrally controlled multi-patient dialysis treatment system for one or more patients' dialysis treatments.

For achieving this object, in the first aspect, provided is a centrally controlled multi-patient dialysis treatment system, comprising: a dialysate preparation unit configured to prepare a dialysate based on a prescription and control dialysate delivery for dialysis treatments in progress; one or more dialysate modules configured to deliver the dialysate to a dialyzer and control an ultrafiltration process; and one or more patient modules configured to control an extracorporeal blood flow through the dialyzer for the dialysis treatment, wherein the dialysate preparation unit, the dialysate modules and the patient modules are configured to be adapted to be assembled into an integrated dialysis treatment system suitable for one or more patients.

According to an optional embodiment of the present disclosure, the dialysate preparation unit is fluidly connected with the dialysate modules, which dialysate preparation unit comprises any one or more of: a heating module configured to heat the dialysate up to around 35 degree centigrade; a dearation module configured to remove air from treated water; a concentrate preparation module configured to prepare liquid concentrates from at least one concentrate cartridge in form of powder; a proportioning unit configured to mix the concentrates with the treated water in a prescribed mixing ratio on demand; and an ETRF disposed before a dialysate distribution loop of the centrally controlled multi-patient dialysis treatment system, and configured to enhance hygiene control.

According to an optional embodiment of the present disclosure, the heating module further comprises any one or more of: a heat exchanger configured to exchange heat from the waste dialysate in a drain piping to the treated water; a pre-heater configured to heat the treated water up to around 35 degree centigrade before the treated water enters the dearation module; and a flow heater installed at an end of the dialysate distribution loop, and configured to keep the dialysate around 35 degree centigrade.

According to an optional embodiment of the present disclosure, the dialysate modules are fluidly communicated with a dialysate distribution loop of the centrally controlled multi-patient dialysis treatment system to distribute the dialysate to the respective patient modules, which dialysate module comprises any one or more of: a dialysis temperature control module configured to control a dialysate temperature; and a balancing system configured to control ultrafiltration in the dialysis treatment with an UF pump, which is further configured to control the ultrafiltration volume in the dialysis treatment.

According to an optional embodiment of the present disclosure, a flow path for the extracorporeal blood flow comprises the dialyzer and a tubing set; and/or the dialysis temperature control module further comprises a dialysate heater disposed ahead of the balancing system, and configured to heat the dialysate to a prescribed treatment temperature and/or for heat disinfection.

According to an optional embodiment of the present disclosure, the dialyzer can be either packaged into the dialysate module or the patient module, preferably by plugging an inlet port and an outlet port of the dialyzer into respective receptacles or dialysate lines.

According to an optional embodiment of the present disclosure, the dialysate preparation unit is configured as a central station to monitor and/or control dialysate preparation parameters of the centrally controlled multi-patient dialysis treatment system and/or treatment status of those patient modules connected in the centrally controlled multi-patient dialysis treatment system.

According to an optional embodiment of the present disclosure, the dialysate preparation unit is configured in a cabinet-shaped form.

According to an optional embodiment of the present disclosure, the dialysate module further comprises a backflow preventer for preventing backflow contamination toward the dialysate distribution loop of the centrally controlled multi-patient dialysis treatment system.

According to an optional embodiment of the present disclosure, the dialysate module further comprises a pressure regulator for maintaining a stable loading pressure to load fresh dialysate into the balancing system so that power drive generated from the stable loading pressure on loading side of the balancing system in the dialysate module can be utilized to simplify hydraulic design.

According to an optional embodiment of the present disclosure, the dialysate module is connected detachably to the dialysate distribution loop by a connector.

According to an optional embodiment of the present disclosure, the patient module further comprises an user interface, preferably a touchscreen for controlling/setting up the respective dialysis treatment.

According to an optional embodiment of the present disclosure, the patient module is configured as a compact device; and/or the patient module is configured to be adapted to be held on a retractable wall mount or a movable stand.

According to an optional embodiment of the present disclosure, the dialysate module and the respective patient module can be integrated as a bedside machine.

According to an optional embodiment of the present disclosure, the centrally controlled dialysis treatment system further comprises a water treatment unit configured to supply the dialysate preparation unit with the treated water.

According to an optional embodiment of the present disclosure, the water treatment unit can be integrated with the centrally controlled multi-patient dialysis treatment system, preferably integrated with the dialysate preparation unit.

According to an optional embodiment of the present disclosure, the centrally controlled multi-patient dialysis treatment system further comprises an additional loop configured to supply the dialysate modules with the treated water to enable the dialysate module to be rinsed and/or disinfected individually.

In the first aspect, provided is an use of the centrally controlled multi-patient dialysis treatment system for one or more patients' dialysis treatments.

For the centrally controlled multi-patient dialysis treatment system, in contrast to the conventional in-center dialysis infrastructures, in addition to cost saving, it is highly space efficient. Moreover, the centrally controlled multi-patient dialysis treatment system is robust and easy to setup.

BRIEF DESCRIPTION OF THE DRAWINGS

The disclosure and advantages thereof will be further understood by reading the following detailed description of some preferred exemplary embodiments with reference to the drawings in which.

DETAILED DESCRIPTION OF PREFERRED EMBODIMENTS

Some exemplary embodiments of the present disclosure will be described hereinafter in more details with reference to the drawings to better understand the basic concept of the disclosure.

Figure 1:
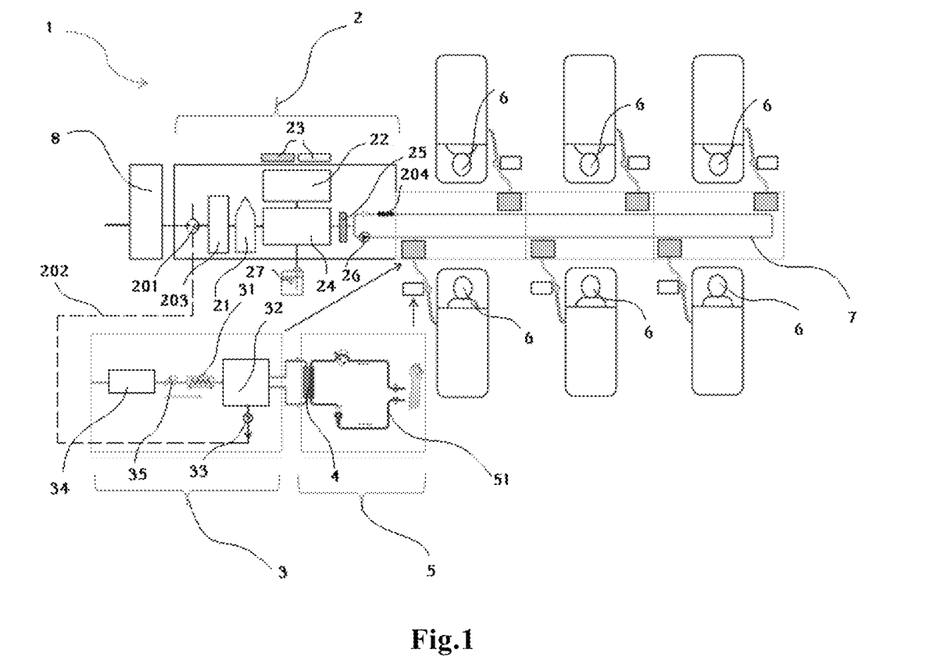
FIG. 1 schematically shows a centrally controlled multi-patient dialysis treatment system according to an exemplary embodiment of the present disclosure in a block diagram.

FIG. 1 schematically shows a centrally controlled multi-patient dialysis treatment system according to an exemplary embodiment of the present disclosure in a block diagram.

As shown in FIG. 1, the centrally controlled multi-patient dialysis treatment system 1 mainly comprises a dialysate preparation unit 2 configured to prepare a dialysate based on a prescription and control dialysate delivery for dialysis treatments in progress; one or more dialysate modules 3 configured to deliver the dialysate to a dialyzer 4 and control an ultrafiltration process; and one or more patient modules 5 configured to control an extracorporeal blood flow through the dialyzer 4 for the dialysis treatment, wherein the dialysate preparation unit 2, the dialysate modules 3 and the patient modules 5 are configured to be adapted to be assembled into an integrated dialysis treatment system suitable for one or more patients 6.

The integrated dialysis treatment system as a single equipment can be disposed in an independent space, for example disposed directly in a treatment area and thus is space-efficient, which even allows for being disposed in a bus to serve small group of patients in remote area. Furthermore, the integrated dialysis treatment system can be installed quickly to meet rapidly growing market demand and a plurality of such systems can be installed independently to meet higher treatment capacity requirements. In addition, the integrated dialysis treatment system can be operated and/or maintained as simple as a single machine.

The dialysate preparation unit 2 is fluidly connected with the dialysate modules 3 preferably by a dialysate distribution loop 7 to supply the dialysate modules 3 with the dialysate.

According to an exemplary embodiment of the present disclosure, the dialysate preparation unit 2 may comprise any one or more of: a heating module configured to heat the dialysate up to a predetermined temperature, for example around 35 degree centigrade; a dearation module 21 configured to remove air from treated water; a concentrate preparation module 22 configured to prepare liquid concentrates from at least one concentrate cartridge 23 in form of powder; a proportioning unit 24 configured to mix the concentrates with the treated water in a prescribed mixing ratio on demand; and an ETRF 25 disposed before the dialysate distribution loop 7 and configured to enhance hygiene control. Preferably, the dialysate preparation unit 2 comprises all of the above parts.

According to an exemplary embodiment of the present disclosure, the heating module further comprises any one or more of: a heat exchanger 201 configured to exchange heat from the waste dialysate in a drain piping 202 to the treated water (the drain piping 202 is shown in a dashed line in FIG. 1); a pre-heater 203 configured to heat the treated water up to a predetermined temperature, for example around 35 degree centigrade, before the treated water enters the dearation module 21; and a flow heater 204 installed at an end of the dialysate distribution loop 7, and configured to keep the dialysate at a predetermined temperature, for example around 35 degree centigrade, in the dialysate distribution loop 7. Preferably, the heating module comprises all of the above parts.

The heat exchanger 201 allows for recovering waste heat from the waste dialysate, thereby improving energy efficiency of the entire system.

The pre-heater 203 is disposed downstream of the heat exchanger 201 such that the pre-heater 203 may be controlled based on the temperature of the treated water after being heated by the heat exchanger 201. Further, the pre-heater 203 is disposed upstream of the dearation module 21 to facilitate controlling the temperature of the treated water to remove air from the treated water more efficiently.

As also can be seen from FIG. 1, the water flows through the dearation module 21 and then enters the proportioning unit 24. The concentrate preparation module 22 is fluidly connected with the proportioning unit 24 to provide the proportioning unit 24 with the prepared liquid concentrates.

The liquid concentrates are prepared from at least one dry power cartridges as described above such that labor and space required for handing and storing can be saved.

As an alternative embodiment, the concentrates can be provided directly from concentrate containers or a central delivery system (CDS) in a liquid form. In the condition of this embodiment, the concentrate preparation module 22 could be omitted.

According to an exemplary embodiment of the present disclosure, the amount of the dialysate to be generated by the proportioning unit 24 may be based on signal feedback from individual patient modules 5.

According to an exemplary embodiment of the present disclosure, a flow pump 26 may be disposed in the dialysate distribution loop 7 to produce high speed circulation flow and a holding pressure to load the fresh dialysate into the dialysate modules 3. The holding pressure may be such that fresh dialysate flow power drive in the dialysate modules 3 is eliminated.

The dialysate distribution loop 7 can either be custom installed on site or pre-installed inside a pre-fabricated cubical to make an installation process simple and quick.

As further shown in FIG. 1, a disinfectant canister 27 is fluidly connected with the proportioning unit 24 such that chemical disinfectant stored in the disinfectant canister 27 can be supplied to the proportioning unit 24 as desired to carry out system disinfection.

According to an exemplary embodiment of the present disclosure, the dialysate preparation unit 2 is configured as a central station to monitor and/or control dialysate preparation parameters of the centrally controlled multi-patient dialysis treatment system 1 and/or treatment status of those patient modules connected in the centrally controlled multi-patient dialysis treatment system 1. The central station comprises a central monitor display by which not only the dialysate preparation unit 2 can be controlled, but also all treatments in progress can be monitored.

Figure 6:
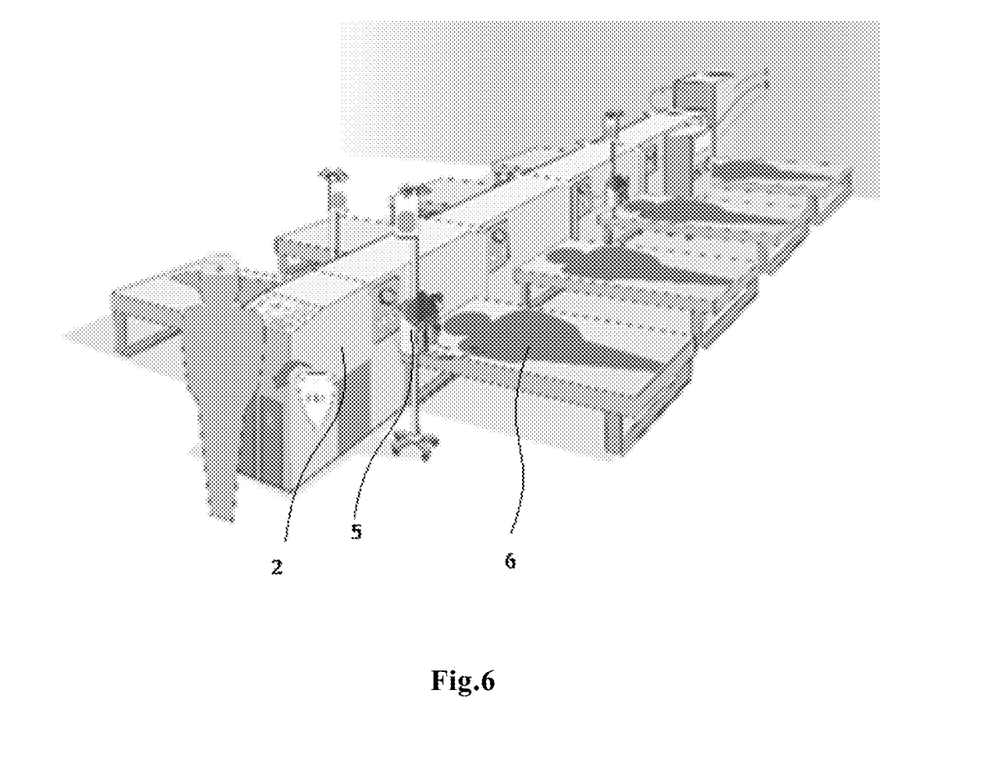
FIG. 6 shows an exemplary actual embodiment of the centrally controlled multi-patient dialysis treatment system.

According to an exemplary embodiment of the present disclosure, the dialysate preparation unit 2 is configured in a cabinet-shaped form (which is shown in FIG. 6 below).

According to an exemplary embodiment of the present disclosure, the dialysate modules 3 are fluidly communicated with the dialysate distribution loop 7 to distribute the dialysate to the respective patient modules 5, wherein the dialysate module 3 may comprise any one or more of a dialysis temperature control module 31 configured to control a dialysate temperature of dialysate flow, and a balancing system 32 configured to control ultrafiltration in the dialysis treatment with an ultrafiltration (UF) pump 33, which is further configured to control the ultrafiltration volume in the dialysis treatment. Preferably, the dialysate module 3 comprises all of the above parts.

According to an exemplary embodiment of the present disclosure, the dialysis temperature control module 31 further comprises a dialysate heater disposed ahead of the balancing system 32, and configured to heat the dialysate to a prescribed treatment temperature and/or for heat disinfection, in particular independently of use of reverse osmosis water through a separate treated water loop.

According to an exemplary embodiment of the present disclosure, the dialysate module 3 further comprises a backflow preventer 34 for preventing backflow contamination toward the dialysate distribution loop 7. Preferably, the backflow preventer 34 is disposed in a dialysate inlet flow path of the dialysate module 3.

According to an exemplary embodiment of the present disclosure, the backflow preventer 34 is fluidly communicated with dialysate distribution loop with robust backward flow isolation means.

According to an exemplary embodiment of the present disclosure, the dialysate module 3 further comprises a pressure regulator 35 for maintaining a stable loading pressure required in an inlet path toward the balancing system. Preferably, the pressure regulator 35 is disposed downstream of the backflow preventer 34. Such a concept can eliminate a flow pump for loading the fresh dialysate into balancing chambers of the balancing system 32 and thus can achieve a simplified design.

According to an exemplary embodiment of the present disclosure, the dialysate module 3 is connected detachably to the dialysate distribution loop 7 by a connector, which will further simplify the installation and maintenance process.

In the dialysis treatment, blood of the patient 6 flows between the dialyzer 4 and the patient 6 via a tubing set. Therefore, a flow path for the extracorporeal blood flow comprises the dialyzer 4 and the tubing set.

Figure 2:
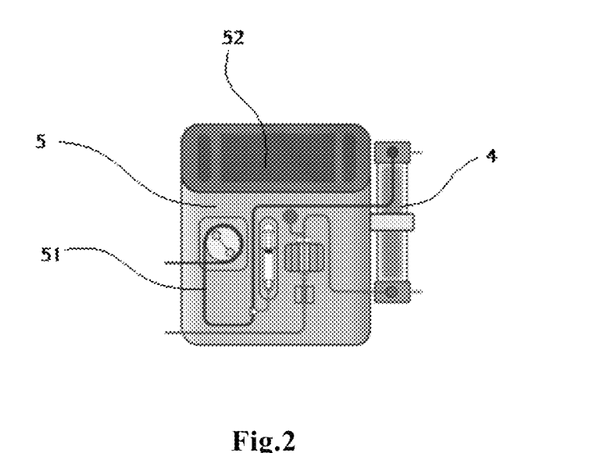
FIG. 2 shows an exemplary embodiment of a patient module into which a dialyzer is packaged.

According to an exemplary embodiment of the present disclosure, as shown in FIG. 1, the patient module 5 comprises an extracorporeal circuit 51. In this embodiment, the dialyzer 4 is packaged into the patient module 5. Dialysate ports of the dialyzer 4 are connected to the dialysate module via a pair of dialysate lines. FIG. 2 shows such an exemplary embodiment.

As further shown in FIG. 2, the patient module 5 further comprises an user interface 52, preferably a touchscreen for controlling/setting up the respective dialysis treatment.

According to an exemplary embodiment of the present disclosure, the touchscreen is embodied with a graphical user interface to control/set up the respective dialysis treatment more easily.

According to an exemplary embodiment of the present disclosure, the patient module 5 is configured as a compact device. The compact device may be configured to be adapted to be held on a retractable wall mount or a movable stand. Such design allows it to be closer to the patients 6, thereby reducing bloodline length.

According to an exemplary embodiment of the present disclosure, the patient module 5 has a built-in, back-up battery in case of power loss.

Except for the dialyzer 4, the patient module 5 has no contact with the dialysate such that no disinfection is needed and just a hygiene wipe-down is sufficient between uses.

To enhance hygiene control, the dialysate distribution loop 7 and connections to the dialysate modules 3 are made as short as possible. Hence, the dialysate preparation unit 2 is kept to have a capacity that is feasible to set up and operate a plurality of dialysis machines. A typical length of the dialysate distribution loop 7 for a capacity to treat 8 patients is around 15 meters. The ETRF 25 is used to serve high flux dialysis treatments in parallel. Defective dialysate module 3 can be easily exchanged with another one to minimize downtime. If the centrally controlled multi-patient dialysis treatment system 1 has run for a long time with small or no dialysate consumption, the dialysate in hydraulic paths would be refreshed in a predetermined manner.

According to an exemplary embodiment of the present disclosure, as shown in FIG. 1, the centrally controlled multi-patient dialysis treatment system 1 further comprises a water treatment unit 8 configured to supply the dialysate preparation unit 2 with the treated water.

According to an exemplary embodiment of the present disclosure, the water treatment unit 8 can be integrated with the centrally controlled multi-patient dialysis treatment system 1, preferably integrated with the dialysate preparation unit 2.

Figure 3:
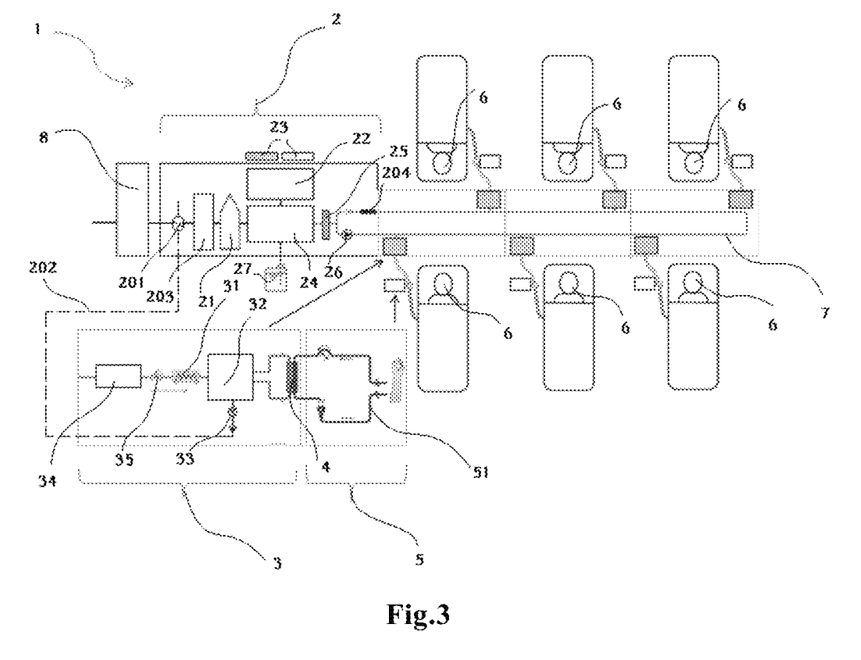
FIG. 3 schematically shows a centrally controlled multi-patient dialysis treatment system according to another exemplary embodiment of the present disclosure in a block diagram, which is similar to FIG. 1, but the dialyzer is packaged into a dialysate module.

FIG. 3 schematically shows a centrally controlled multi-patient dialysis treatment system according to another exemplary embodiment of the present disclosure in a block diagram, which is similar to FIG. 1, but the dialyzer 4 is packaged into the dialysate module 3, preferably by plugging an inlet port and an outlet port of the dialyzer into respective receptacles or dialysate lines.

Such a design eliminates dialysate line connected with the dialyzer 4, which not only enhances operational efficiency, but also further improves the hygiene control. With smaller fluid volume and less exposure to heat loss, temperature control and heat disinfection process can be more efficient.

Figure 4:
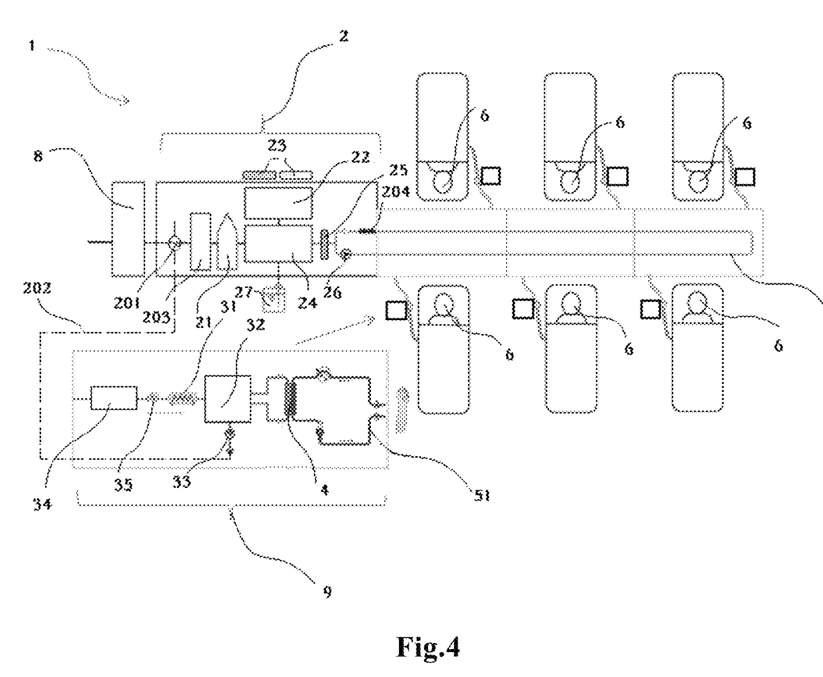
FIG. 4 schematically shows a centrally controlled multi-patient dialysis treatment system according to a still exemplary embodiment of the present disclosure in a block diagram, which is similar to FIG. 1 and FIG. 3, but the dialysate module and the respective patient module are integrated as a compact bedside machine.

FIG. 4 schematically shows a centrally controlled multi-patient dialysis treatment system according to a still exemplary embodiment of the present disclosure in a block diagram, which is similar to FIG. 1 and FIG. 3, but the dialysate module and the respective patient module is integrated as a compact bedside machine 9.

Figure 5:
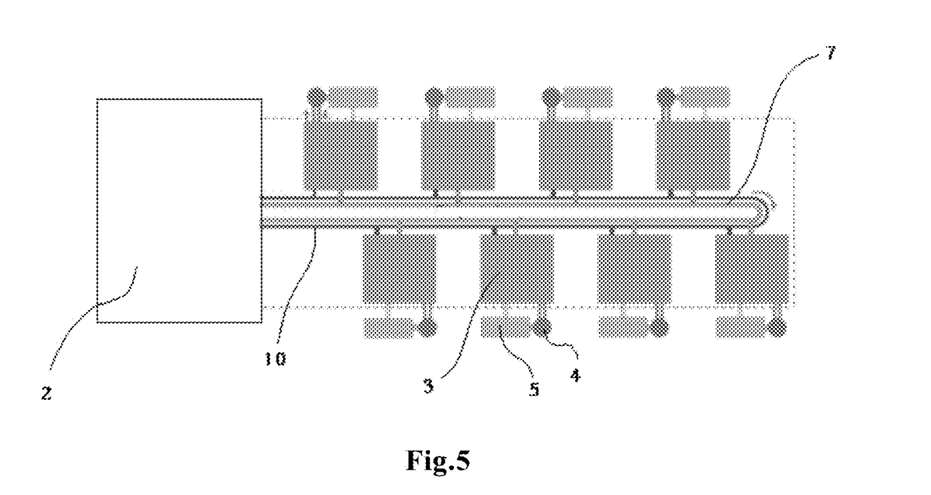
FIG. 5 schematically shows only a portion of a centrally controlled multi-patient dialysis treatment system according to another exemplary embodiment of the present disclosure in a block diagram.

FIG. 5 schematically shows only a portion of a centrally controlled multi-patient dialysis treatment system according to another exemplary embodiment of the present disclosure in a block diagram. As shown in FIG. 5, the centrally controlled multi-patient dialysis treatment system 1 further comprises an additional loop 10 configured to supply the dialysate modules 3 with the treated water to enable the dialysate module 3 to be rinsed and/or disinfected individually. Preferably, the additional loop 10 runs in parallel with the dialysate distribution loop 7.

In addition, the dialysate module 3 can suck chemical disinfectant via either a disinfectant port or a built-in refillable disinfectant cartridge. An internal heater may be provided to heat up fluid in the hydraulic paths to a temperature required for a disinfection process.

According to an exemplary embodiment of the present disclosure, the centrally controlled multi-patient dialysis treatment system 1 can be configured as shown in FIG. 6. As shown in FIG. 6, the centrally controlled multi-patient dialysis treatment system 1 is an all-in-one dialysis treatment system from a reverse osmosis filter to bedside treatment devices. The system can treat a plurality of patients via connected treatment modules. The skilled person in the art may understand that while the patient module 5 is shown in FIG. 6 to be held on a movable stand acting as a holder for holding the patient module 5, the patient module 5 may also be held on a retractable wall mount, as described above, which does not depart from the technical idea of the present application, for example as shown in FIG. 1 and FIG. 3. By integrating some core functional hydraulic components of a dialysis machine into a central unit, slim-structured treatment module can be realized at low cost. In contrast to the conventional in-center dialysis infrastructures, in addition to cost saving, it is highly space efficient. Moreover, the centrally controlled multi-patient dialysis treatment system 1 is robust and easy to setup.

While certain embodiments have been described, these embodiments have been presented by way of example only, and are not intended to limit the scope of the disclosure. The attached claims and their equivalents are intended to cover all the modifications, substitutions and changes as would fall within the scope and spirit of the disclosure.

The invention claimed is:

1. A centrally controlled multi-patient dialysis treatment system, comprising:
    a dialysate preparation unit configured to prepare a dialysate based on a prescription and control dialysate delivery for dialysis treatments in progress;
    two or more dialysate modules, each of the two or more dialysate modules configured to deliver the dialysate to a dialyzer and control an ultrafiltration process; and
    two or more patient modules, each of the two or more patient modules configured to control a corresponding extracorporeal blood flow through the dialyzer for a corresponding dialysis treatment of the dialysis treatments,
    wherein the dialysate preparation unit, the two or more dialysate modules, and the two or more patient modules are configured to be adapted to be assembled into an integrated dialysis treatment system suitable for two or more patients,
    wherein the dialysate preparation unit is fluidly connected to the two or more dialysate modules via a dialysate distribution loop that supplies the two or more dialysate modules with the dialysate,
    wherein an inlet and an outlet of the dialysate distribution loop are connected to an endotoxin retentive filter (ETRF), and
    wherein the dialysate preparation unit is configured as a central station to (i) control dialysate preparation parameters of the centrally controlled multi-patient dialysis treatment system and (ii) monitor a treatment status of the two or more patient modules in the centrally controlled multi-patient dialysis treatment system.

2. The centrally controlled multi-patient dialysis treatment system according to claim 1, wherein the dialysate preparation unit is fluidly connected with the two or more dialysate modules, and wherein the dialysate preparation unit comprises any one or more of:
   a heating module configured to heat the dialysate up to around 35 degree centigrade;
   a deaeration module configured to remove air from treated water;
   a concentrate preparation module configured to prepare liquid concentrates from at least one concentrate cartridge in form of powder;
   a proportioning unit configured to mix the liquid concentrates with the treated water in a prescribed mixing ratio on demand; and
   the ETRF configured to enhance hygiene control.

3. The centrally controlled multi-patient dialysis treatment system according to claim 2, wherein the heating module further comprises any one or more of:
   a heat exchanger configured to exchange heat from waste dialysate in a drain piping to the treated water;
   a pre-heater configured to heat the treated water up to around 35 degree centigrade before the treated water enters the deaeration module; and
   a flow heater installed at an end of the dialysate distribution loop, and configured to keep the dialysate around 35 degree centigrade.

4. The centrally controlled multi-patient dialysis treatment system according to claim 1, wherein the two or more dialysate modules are fluidly communicated with the dialysate distribution loop of the centrally controlled multi-patient dialysis treatment system to distribute the dialysate to the two or more patient modules, each of the two or more dialysate modules comprising at least one of:
   a dialysis temperature control module configured to control a dialysate temperature; and
   a balancing system configured to control ultrafiltration in the corresponding dialysis treatment with a UF pump, which is further configured to control ultrafiltration volume in the corresponding dialysis treatment.

5. The centrally controlled multi-patient dialysis treatment system according to claim 4, wherein
   a flow path for the extracorporeal blood flow comprises the dialyzer and a tubing set; and/or
   the dialysis temperature control module further comprises a dialysate heater disposed ahead of the balancing system, and configured to heat the dialysate to a prescribed treatment temperature and/or for heat disinfection.

6. The centrally controlled multi-patient dialysis treatment system according to claim 1, wherein
   the dialyzer can be either packaged into the two or more dialysate modules or the two or more patient modules by plugging an inlet port and an outlet port of the dialyzer into respective receptacles or dialysate lines.

7. The centrally controlled multi-patient dialysis treatment system according to claim 1, wherein the dialysate preparation unit is configured in a cabinet-shaped form.

8. The centrally controlled multi-patient dialysis treatment system according to claim 1, wherein each of the two or more dialysate modules further comprises:
   a backflow preventer for preventing backflow contamination toward the dialysate distribution loop of the centrally controlled multi-patient dialysis treatment system.

9. The centrally controlled multi-patient dialysis treatment system according to claim 4, wherein each of the two or more dialysate modules further comprises:
   a pressure regulator for maintaining a stable loading pressure to load fresh dialysate into the balancing system so that power drive generated from the stable loading pressure on a loading side of the balancing system can be utilized to simplify hydraulic design.

10. The centrally controlled multi-patient dialysis treatment system according to claim 4, wherein each of the two or more dialysate modules is connected detachably to the dialysate distribution loop by a connector.

11. The centrally controlled multi-patient dialysis treatment system according to claim 1, wherein each of the two or more patient modules further comprises:
    a user interface that includes a touchscreen for controlling or setting up the respective dialysis treatment.

12. The centrally controlled multi-patient dialysis treatment system according to claim 1, wherein each of the two or more patient modules is configured to be adapted to be held on a retractable wall mount or a movable stand.

13. The centrally controlled multi-patient dialysis treatment system according to claim 1, wherein the two or more dialysate modules and the two or more patient modules can be integrated as a bedside machine.

14. The centrally controlled multi-patient dialysis treatment system according to claim 1, further comprising:
    a water treatment unit configured to supply the dialysate preparation unit with treated water.

15. The centrally controlled multi-patient dialysis treatment system according to claim 14, wherein the water treatment unit can be integrated with the centrally controlled multi-patient dialysis treatment system by means of a connection between the water treatment unit and the dialysate preparation unit.

16. The centrally controlled multi-patient dialysis treatment system according to claim 1, further comprising:
    an additional loop configured to supply the two or more dialysate modules with treated water to enable the two or more dialysate modules to be rinsed and/or disinfected individually.

17. The centrally controlled multi-patient dialysis treatment system according to claim 2, wherein the dialyzer can be either packaged into the two or more dialysate modules or the two or more patient modules by plugging an inlet port and an outlet port of the dialyzer into respective receptacles or dialysate lines.

* * * * *